(12) United States Patent
Chiao et al.

(10) Patent No.: US 8,455,827 B1
(45) Date of Patent: Jun. 4, 2013

(54) METHOD AND APPARATUS FOR DETERMINING THE WATER CONTENT OF ORGANIC SOLVENT SOLUTIONS

(75) Inventors: James Chiao, San Jose, CA (US); Charles A. Reichel, Fremont, CA (US); Michael R. Van Tuyl, San Jose, CA (US)

(73) Assignee: EDC Biosystems, Inc., Fremont, CA (US)

( * ) Notice: Subject to any disclaimer, the term of this patent is extended or adjusted under 35 U.S.C. 154(b) by 272 days.

(21) Appl. No.: 12/975,233

(22) Filed: Dec. 21, 2010

(51) Int. Cl.
*G01J 5/02* (2006.01)
(52) U.S. Cl.
USPC ...................................... 250/339.01; 250/343
(58) Field of Classification Search
USPC ............... 250/338.1, 338.5, 339.01, 339.06, 250/339.1, 341.1, 343
See application file for complete search history.

(56) References Cited

U.S. PATENT DOCUMENTS

| | | | |
|---|---|---|---|
| 5,886,348 A * | 3/1999 | Lessure et al. | 250/339.13 |
| 6,421,614 B1 | 7/2002 | Goldman et al. | |
| 7,564,046 B1 | 7/2009 | Hoang | |
| 7,688,448 B2 | 3/2010 | Bamberg et al. | |
| 2009/0097507 A1 * | 4/2009 | Zhu et al. | 372/6 |

OTHER PUBLICATIONS

David J. Semin, Tim J. Malone, Matthew T. Paley and Peter W. Woods, A Novel Approach to Determine Water Content in DMSO for a Compound Collection Repository, Journal of Biomolecular Screening, 2005, vol. 10(6), pp. 568-572.
Michael J. Pelletier and Mario L. Fabilli, Rapid, Nondestructive Near-Infrared Assay for Water in Sealed Dimethyl Sulfoxide Compound Repository Containers, Applied Spectroscopy, 2007, vol. 61(9), pp. 935-939.
OZ Optics, Laser Diode Collimators, www.ozoptics.com, Feb. 22, 2005.
R. Ellson, R. Stearns, M. Mutz, C. Brown, B. Browning, D. Harris, S. Qureshi, J. Shieh and D. Wold, In situ DMSO Hydration Measurements of HTS Compound Libraries, Abstract from PubMed, PMID 16178808, 2005.

* cited by examiner

*Primary Examiner* — Mark R Gaworecki
(74) *Attorney, Agent, or Firm* — Donald J. Pagel

(57) ABSTRACT

A method and apparatus for determining the amount of water in an organic solvent solution, such as a DMSO solution. The apparatus comprises an infrared LED for emitting near infrared light; a laser diode collimator for forming a collimated light beam from the light emitted by the LED; a sample container holder for accepting a sample container containing a sample solution; a photodiode for generating an output signal that is related to the intensity of the collimated light beam after the collimated light beam has passed through the sample solution; and a control means for controlling the stability of the near infrared light emitted by the infrared LED by controlling an amount of current flowing through the infrared LED.

Figure 1:
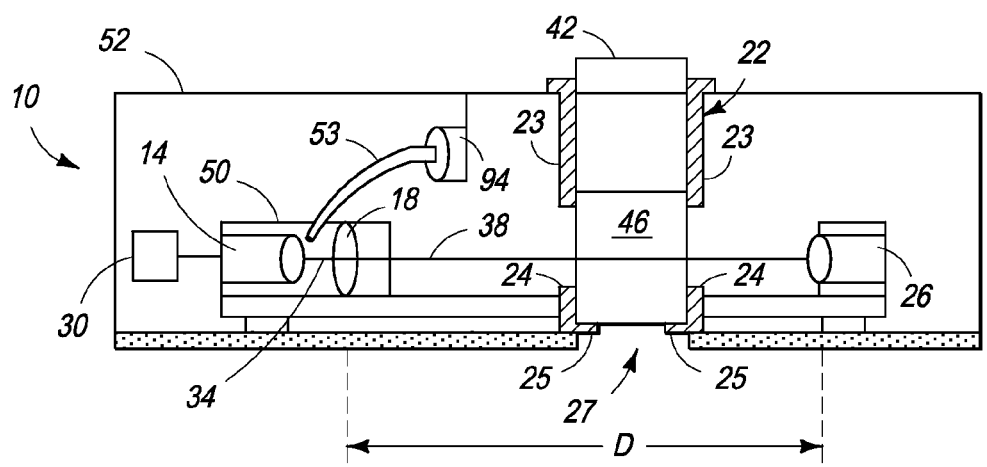

19 Claims, 2 Drawing Sheets

METHOD AND APPARATUS FOR DETERMINING THE WATER CONTENT OF ORGANIC SOLVENT SOLUTIONS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

REFERENCE TO A SEQUENCE LISTING

Not Applicable

BACKGROUND OF THE INVENTION

The screening of large numbers of chemical compounds bfor pharmaceutical, toxicological, genetic or other types of activity is a technique that is widely used by scientists and researchers. For example, in searching tbr compounds that might have usefulness as new drugs, a researcher may want to determine if a compound shows any sign of binding to or reacting with another biological molecule, so as to decrease or increase the activity of the biomolecule. This type of screening is used, for example, in small-molecule drug discovery.

To do this, the researcher needs to evaluate how one or more test compounds react with a large number of target compounds. This means that pharmaceutical companies, universities and other research organizations need to maintain very large libraries of target compounds for high throughput screening. The library size can range from the low hundreds of thousands to tens of millions of chemical compounds. Each of these compounds must be cataloged, stored, sampled, distributed and tracked. Not only are the logistics of tracking a large chemical library challenging, but the quality of the chemical samples in the library must also be monitored.

Initially, the individual compounds in the chemical library are usually obtained as solids, films or beads. A master copy of the compound is then prepared as a concentrated solution in an organic solvent, which is usually dimethyl sulfoxide (DMSO), and is stored in a compound storage tube. Replicates (or daughters) of the master copy are prepared and distributed to end users. The end user may consider the daughter solution as a local master and prepare a low volume working copy of the compound by transferring a small volume of the local master to another storage container, such as a polypropylene microtube or microplate. The concentration of the compound in the working copy could be, for example, ten millimolar (10 mM) for small molecule compounds, or 200 mM for fraction libraries. Small volumes of the working copy of the compound are constantly removed from the storage container as the researcher prepares samples for use in an assay. This use exposes the working copy to common laboratory contaminants such as light, water vapor, dust and oxygen, and gradually causes the quality and/or concentration of the working copy to change.

Water vapor is a major problem for samples stored in DMSO. DMSO is very hygroscopic, and it is not unusual for the concentration of working copies to decrease by as much as 20% or more while being used because of water dilution. Water uptake by DMSO also causes freezing point depression, which can cause quicker degradation of samples when being stored at low temperatures. Consequently, it is necessary to periodically check the working sample to determine the concentration of water in the working sample.

Several methods for determining the water content (hydration) of DMSO are known in the prior art. An older method is the Karl Fischer titration technique. Newer methods include acoustic methods and optical methods, such as fluorescence techniques and absorption techniques. For example, an optical approach to determining the water content in DMSO for a corporate compound collection is described in Semin et al., A Novel Approach to Determine Water Content in DMSO for a Compound Collection Repository. *Journal of Biomolecular Screening* 10(6), pp. 568-572 (2005). This approach uses near-infrared (NIR) spectroscopy to analyze the absorption bands of water present in the DMSO. This approach is desirable because it is accurate and nondestructive. However, the instrumentation used in this technique, especially the spectrometer, means that it is relatively expensive and not easily integrated into a lab automation system.

What is needed is a technique for measuring the water content in DMSO solutions or other organic solvent solutions that is easily integrated into a lab instrument, a handheld device or an automation system while being inexpensive, last and having low power requirements. Additionally, the measurements should be taken directly in the storage vessel holding the DMSO or other solvent solution without destroying or contaminating any of the solution.

SUMMARY OF THE INVENTION

Briefly, the present invention comprises a method and apparatus for nondestructively determining the amount of water in an organic solvent solution, such as a DMSO solution in a compound storage tube or other sample container. The apparatus comprises an infrared light emitting diode (LED) for emitting near infrared light (NIR); a laser diode collimator for forming a collimated light beam from the light emitted by the LED; a holder for keeping a sample tube or other compound storage container in a fixed space; a photodiode for generating an output signal that is related to the intensity of the collimated light beam after the collimated light beam has passed through the solution held in the sample container; and a control means for controlling the stability of the light emitted from the LED.

BRIEF DESCRIPTION OF TI-IE SEVERAL VIEWS OF THE DRAWINGS

Figure 2:
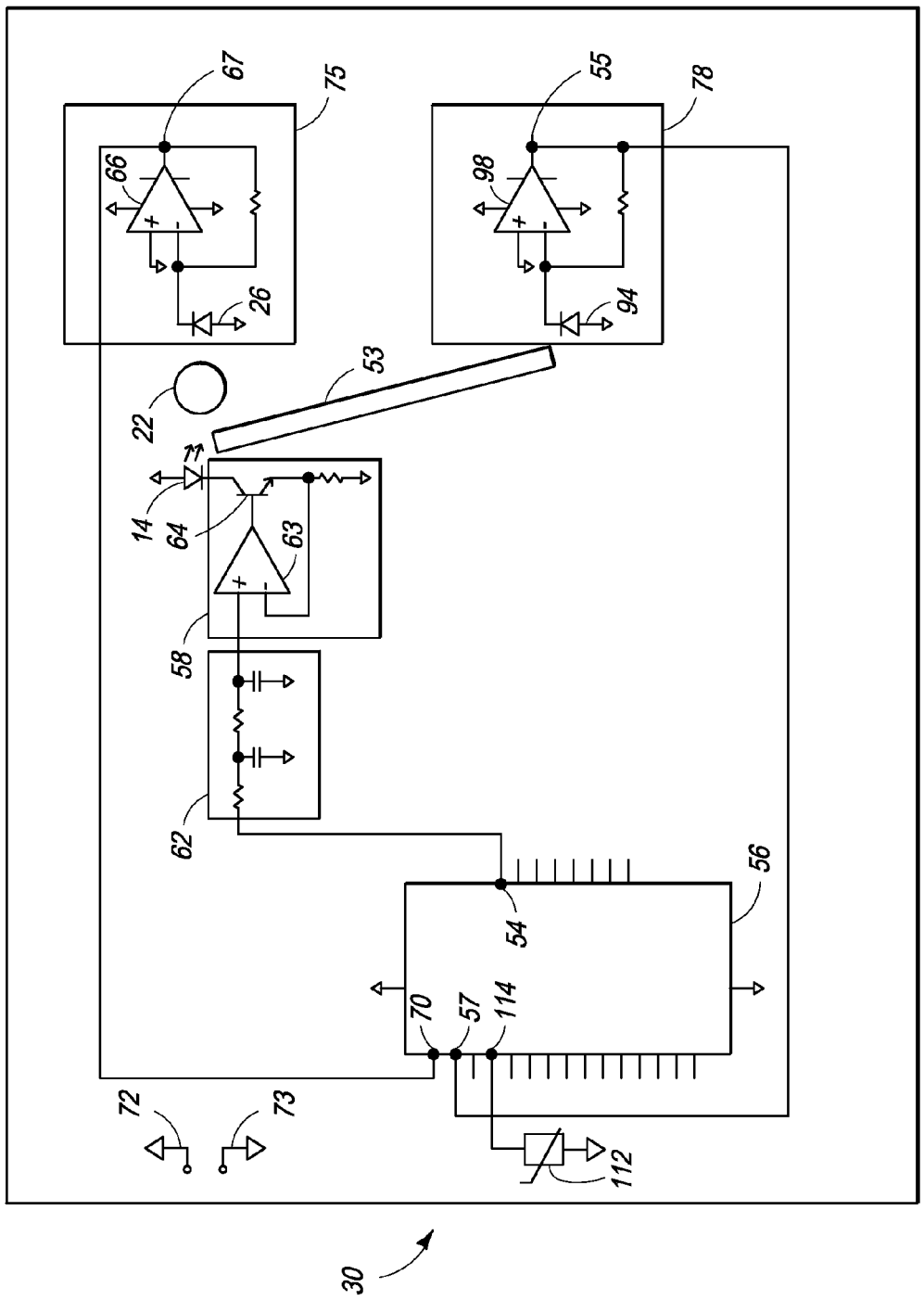

FIG. 1 is a block diagram of an apparatus according to the present invention; and FIG. 2 is a circuit diagram of the apparatus according to the present invention.

DETAILED DESCRIPTION OF THE INVENTION

FIG. 1 illustrates a low power apparatus 10 for determining the water content in a solution comprised of an organic solvent such as dimethyl sulfoxide (DMSO). The apparatus 10 is comprised of an infrared (IR) light emitting diode (LED) 14, a laser diode collimator 18, a sample container holder 22, a first photodiode 26 and an electronics block 30. A light pipe 53 and a second photodiode 94 are also illustrated in FIG. 1. An emission of light 34 is emitted by the LED 14 and passes through the laser diode collimator 18. A collimated light beam 38 exits the collimator 18 and traverses a distance "D" to the first photodiode 26. In operation, a sample container 42 containing a sample solution 46 is positioned in the sample container holder 22 so that the collimated light beam 38 passes through the sample container 42 and the sample solution 46 before striking the first photodiode 26 without striking the sample container holder 22.

The LED 14 and the collimator 18 may be mounted inside of a mounting tube 50, and the entire apparatus 10 can be enclosed within a housing 52. The housing 52 reduces the small effect of ambient light on the detection system and protects the electronic and optical components from interference (physical jarring), dirt and moisture. The distance "D" exists between the collimator 18 and the photodiode 26. The light pipe 53 samples light from the LED 14 and conveys the light to the photodiode 94 described below with respect to FIG. 2.

The light pipe 53 comprises a tube capable of conducting near inli-ared (NIR) light over at least short distances. NIR light is light having a wavelength in the range of approximately 780 nm to 3000 nm. In a preferred embodiment, the light pipe has an outer diameter of approximately 3.0 mm and is comprised of a solid molded plastic, such as polycarbonate or poly (methyl methacrylate), also known as PMMA, or of other plastics or materials. A commercially available light pipe sold by the company BIVAR, of Irvine, Calif. under the product series designation PLP2-XXX, is suitable for use as the light pipe 53. Another commercially available light pipe that can be used is sold by Industrial Fiber Optics, under the product designation CK-120.

In the preferred embodiment, the light pipe 53 is connected to the second photodiode 94 using an optical gel having an index of refraction that matches the index of rel-action of the light pipe 53. For example, an optical gel provided by Nye Lubricants. Inc. of Fairhaven, Mass., under the product designation Smartgel OC-459 is acceptable for this purpose, as is the product Smartgel OC-440. The Smartgel OC-459 product has an index of refraction of approximately 1.57 at 1450 nm which closely matches the index of refraction of a polycarbonate light pipe.

Some commercially available light pipes, such as the PLP2-XXX series of light pipes, are provided with a lens formed on one end of the light pipe and a flat surface at the other end. In the preferred embodiment, the light pipe 53 does not include a lens at either end because the lens tends to diffuse light. Rather, it is preferred that the light pipe 53 be flat at both the end next to the LED 14 and at the end next to the detector 94. In the case of the PLP2-XXX series of light pipes, this is accomplished by grinding off the lens and polishing the end to yield the desired flat end. In other embodiments, the light pipe 53 can include the lens, with the lens end generally being positioned next to the LED) 14.

The sample container holder 22 is positioned between the LED 14 and the first to photodiode 26 for accepting the sample container 42. Preferably, the sample container holder 22 is just a member of adequate size to firmly hold the sample container 42 when the sample container 42 has an outer diameter (OD) of a given size. The sample container holder 22 is designed so that the collimated beam 38 does not strike the sample container holder 22. In the preferred embodiment, the sample container holder 22 includes an upper piece 23 and a separate lower piece 24, both of which are comprised of a plastic, such as Delrin™ brand polyoxymethylene. However, other materials, such as aluminum, can be used to construct the sample container holder 22. The upper piece 23 is a block of material with a hole drilled through it to accommodate the sample container 42 having a given outer diameter.

To accommodate sample containers having different sized outer diameters, the upper piece 23 can be removed and replaced with a new upper piece 23 having hole with a diameter that is appropriate for accommodating the OD of the new sample container 42. The lower piece 24 is a block of material with a hole drilled through it to accept the sample container 42. The lower piece 24 may include a restraining edge 25 to support the bottom of the sample container 42 and to keep the sample container 42 from extending out of the housing 52 through a hole 27 in the housing 52. Alternatively, in other embodiments, the restraining edge is absent to allow the sample container 42 to pass through the hole 27 in the bottom of the housing 52. In most cases, the hole 27 in the housing 52 is covered to prevent ambient light from entering through the hole 27.

FIG. 2 illustrates the electrical configuration of the apparatus 10. FIG. 2 includes the components contained in the electronics block 30. The LED 14, the sample container holder 22, the photodiodes 26 and 94 and the light pipe 53 discussed in FIG. 1 are also illustrated in FIG. 2. The intensity of the light emitted by the LED 14 is controlled by the amount of current flowing through the LED 14. When the light emitted by the LED 14 strikes the photodiode 26, a current is generated by the photodiode. This current is related (proportional) to the intensity of the collimated light beam 38 after the collimated light beam has passed through the sample solution 46 and the sample container 42. The current output of the photodiode 26 is connected to a first transimpedance amplifier 66 that generates a voltage output 67 which represents the power of the transmitted light. The voltage output 67 is fed into an analog to digital convertor (ADC) input 70 of the microcontroller 56 to yield a digital value that represents the transmitted power of the light that has passed through the sample container 42 and the solution 46. This digital value is used as the quantity $P_{solution}$ or $P_{solvent}$ in equation 1 described below. The power supply for the apparatus 10 is inputted to the voltage input 72 and ground 73.

It is important to the functioning of the apparatus 10 that the intensity of the light emitted by the LED 14 be stable (i.e. the intensity needs to be constant). To accomplish this stability, the intensity of the light from LED 14 is sampled by the light pipe 53 and converted to a DC voltage by going through the second photodiode 94 and the second transimpedance amplifier 98. The voltage at an output 55 of the transimpedance amplifier 98 is read by a microcontroller 56 at its ADC (analog to digital convertor) input 57. Based on the feedback voltage at the ADC input 57, the microcontroller 56 controls the amount of current flowing through the LED 14 through the use of a pulse width modulation (PWM) controlled current source.

In the preferred embodiment, a PWM signal is generated by PWM control logic within the microcontroller 56 which is connected to a PWM output 54 of the microcontroller 56. A filter 62 is positioned between the microcontroller 56 and a current source 58 to convert the PWM signal to a DC control voltage. The current source 58 is comprised of an operational amplifier 63 and a transistor 64 which function to generate a DC current that is proportional to the DC control voltage generated by the filter 62.

In the preferred embodiment, the microcontroller 56 is an eight bit microcontroller. Eight bit microcontrollers suitable for use as the microcontroller 56 are commercially available from Microchip Technology Inc. under the product designation PIC® Microcontroller, or from ATMEL Corporation under the product designation AVR microcontroller.

The low power apparatus 10 is used to determine the water content in the sample solution 46 by calculating the absorbance of the sample solution 46 at about 1450 nm or 1900 nm. Water has absorption bands at 1450 nm and 1900 nm that can be excited by near IR light from the LED 14, so one or both of these bands can be used for detecting water provided that absorption bands from the solvent or solution do not interfere with both of these bands.

The sample solution 46 is a solution comprised of a 100% pure organic solvent, such as DMSO; the organic solvent plus water; the organic solvent plus one or more dissolved compounds; and/or the organic solvent together with the dissolved compound and water. Since DMSO is the organic solvent most often used in pharmaceutical compound storage situations, the discussion below uses DMSO as the organic solvent. The water content of sample solutions 46 comprised of organic solvents besides DMSO can also be determined using the apparatus 10, provided that the organic solvents or dissolved compounds do not have absorption bands in both the 1450 nm and 1900 nm regions. For example, acetonitrile, hexane and dibutyl ether are some of the other organic solvents in which the water content can be determined using the apparatus 10. Additional organic solvents in which the water content can be determined using the apparatus 10 include methylene chloride and chloroform.

The specific nature of the dissolved compound in the sample solution 46 is not important to the present invention, but the dissolved compounds generally comprise compounds of interest in the biological, pharmaceutical, medical or chemical fields. For example, the target compounds maintained in libraries used in high throughput screening by pharmaceutical companies, universities and other research organizations are typical dissolved compounds. A typical use for the compounds in these libraries is the screening used for small-molecule drug discovery.

In the preferred embodiment, the absorbance (A) of a sample is calculated using equation 1, which is a well known derivation of the Beer-Lambert law:

$$A = \log_{10}(P_{solvent}/P_{solution}) \quad (1)$$

where $P_{solvent}$ is the transmitted power with 100% DMSO in the sample container 42; and $P_{solution}$ is the transmitted power with a DMSO/water solution (or any of the other sample solutions 46 described previously) in the sample container 42.

In order to determine an unknown water content in a DMSO sample, a calibration data set is needed. In the preferred embodiment, the calibration data set is established by using the apparatus 10 to measure the absorbance (A) of a series of calibration samples having different (but known) DMSO/H₂0 concentrations. Each of the DMSO/H₂0 solutions for each calibration sample is contained in the same type of sample container 42 (i.e. the specified type of sample tube).

The calibration data set is generated by measuring the transmitted power for each of is the calibration samples (i.e. $P_{solution}$); the absorbance (A) for the calibration sample is calculated using equation 1; and the absorbance (A) for each calibration sample (along with other relevant data) is stored in an EEPROM associated with the microcontroller 56. In the preferred embodiment, the calibration data set is a list of ordered data entries, with each calibration sample having its own data entry comprised of the DMSO concentration and the quantity $\log_{10}(P_{solvent}/P_{solution})$.

The calibration data set may be retrieved for later use with the specified type of sample container 42. The unknown water concentration and/or the DMSO concentration in an unknown sample solution 46 is obtained by measuring the absorbance (A) of the unknown sample solution 46. An algorithm running on the microcontroller 56 then uses linear interpolation from the stored calibration data set to generate a value for the unknown water concentration and/or the DMSO concentration in the sample solution 46. In the preferred embodiment, DMSO concentration is the value that is generated by the algorithm.

To illustrate this procedure, four sample tubes are used as the calibration data set. These four tubes have DMSO concentrations of 100%, 90%, 80% and 70% by volume, with water making up the rest of the sample (i.e. the tubes have water concentrations of 0%, 10%, 20% and 30%, respectively). Each of the four sample tubes are inserted into the sample container holder 22, one by one, and the $P_{solution}$ value for each sample tube is read and stored as was described previously. The $P_{solvent}$ value in equation 1 is the measurement taken using the 100% DMSO tube. The absorbance values for the four sample tubes are calculated by the microcontroller 56 using equation 1. The water concentration and/or the DMSO concentration in an unknown sample (i.e. the sample solution 46) is obtained by inserting the sample container 42 containing the unknown sample into the sample container holder 22 and measuring the absorbance (A) of the unknown sample (i.e. by measuring $P_{solution}$ for the unknown sample and calculating $\log_{10}(P_{solvent}/P_{solution})$. The unknown water concentration and/or the DMSO concentration are then calculated by the microcontroller 56 using linear interpolation from the stored calibration data set.

In the preferred embodiment, the LED 14 comprises an infrared LED that emits NIR light having a peak wavelength in the approximate range of 1400-1600 nm, and a bandwidth of approximately 100 nm. More preferably, the LED 14 has a peak wavelength centered at approximate range 1450 nm, and a bandwidth of approximately 100 nm. Because the 1450 nm absorption band of water spans a bandwidth of approximately 1400 nm-1600 nm, an LED with an emission band in the same region can be used as the light source. In other words, the LED 14 preferably has a power spectrum that closely matches one of the absorption bands of the water absorption spectrum in the near infrared region.

Detecting the 1450 nm absorption band of water instead of the 1900 nm band allows the more readily available 1450/1550 nm infrared LEDs to be used as the LED 14, as compared to less readily available 1900 nm infrared LEDs. However, a 1900 nm infrared LED could also be used as the LED 14 because water also has a 1900 nm absorption band. An acceptable 1450 nm infrared LED for use as the LED 14 is the commercially available product LED 1450E, sold by Thorlabs. An acceptable 1900 nm infrared LED has a peak wavelength centered on approximately 1900 nm and a bandwidth of approximately 100 nm. Peak wavelength means the maximum radiated power of the LED is emitted at this wavelength.

The NIR light emitted by the LED 14 passes through the collimator 18 to generate the collimated light beam 38 of NIR light (for purposes of this patent application, the term "light" includes IR radiation, even though IR radiation is not visible light). The collimator 18 comprises a collimating lens, such as the type frequently used with laser diodes. Since the LED 14 is a surface light source, rather than a point light source, the collimated beam 38 is not as well-collimated as the collimated beam that would be obtained from a point light source. Rather, the collimated beam 38 forms an image of the LED light emitting surface at the image plane (the image plane is the plane that contains the object's projected image). Therefore, over a relatively short distance "d" from the lens to the image plane, and slightly beyond, the projected image of the LED light emitting surface is well confined and can be considered to be a roughly collimated beam.

To generate the collimated light beam 38, the LED 14 is chosen to have a viewing half angle roughly matching the numerical aperture of the collimator to avoid under filling or overfilling the lens of the collimator. The LED 14 and the collimator 18 are then attached to the mounting tube 50 to keep the LED 14 and the collimator 18 aligned. In the preferred embodiment, the collimator 18 is a laser diode collimator, such as the laser diode collimator commercially available from Thorlabs, under the product designation of LT110 P-B. The laser diode collimator can be made of glass, acrylic material, or other materials.

In the preferred embodiment, the first photodiode 26 comprises a PIN-type photodiode, with a spectral response covering the desired absorption band. For example, an InGaAs PIN photodiode is acceptable for use in the present invention. Since the 1450 nm absorption band of water covers the range of 1400 nm-1600 mm, the spectral response of the InGaAs PIN photodiode should also cover the 1400 nm to 1600 nm range. Other types of photodiodes, such as PbSe. InSb and HgCdTe (MCT) photodiodes, having an appropriate spectral response can also be used as the first photodiode 26. By choosing an infrared LED that has a power spectrum that matches the absorbance spectra at the wavelength of interest, the LED acts as a matched filter in the frequency domain for the detection channel. Therefore, an optimal signal-to-noise ratio (SNR) is obtained without the use of one or more additional optical filters.

The distance between the collimator 18 and the first photodiode 26 (i.e. the distance D in FIG. 1) is preferably in the range of 5 mm to 60 mm, depending on the size of the sample container 42 and the optical configuration of the apparatus 10, and more preferably is in the range of 10 mm to 25 mm.

Referring to FIG. 2, the current source 58, the LED 14, the microcontroller 56, the filter 62, the first photodiode 26 and the first transimpedance amplifier 66 comprise a first measurement channel. Within the measurement channel, the first photodiode 26 and the first transimpedance amplifier 66 comprise a first detector 75. A second detector 78 comprises the second photodiode 94 and the second transimpedance amplifier 98. The components in the second detector 78 are electrically identical to the components in the first detector 75 (i.e. they exhibit the same electrical behavior).

A feedback channel comprises the light pipe 53, the second photodiode 94 and the second transimpedance amplifier 98. The second photodiode 94 comprises a photodiode of the same type used in the first photodiode 26. The second transimpedance amplifier 98 is electrically identical to the first transimpedance amplifier 66. The light pipe 53 samples NIR light from the LED 14 and conveys it to the second photodiode 94. In this context, sampling means that a portion of the NIR light emitted by the LED 14 is conveyed from one end of the light pipe 53 to the other end. The photodiode 94 then converts the sampled light intensity into a current that is related to the intensity (radiated power) of the light emitted by the infrared LED. The second transimpedance amplifier 98 converts this current into a feedback voltage.

The feedback channel is used to control the source/detector response and stabilize the light emitted by the LED 14. This feedback control is done to minimize the effects of temperature and power supply variations on the apparatus 10. With the microcontroller 56 acting as a controller, the controller reads the radiated power detected by the photodiode 94 with the ADC input 57, and controls the PWM output 54 to set the LED current such that the radiated power from the LED 14 remains at a preset level, despite temperature and/or power supply variations in the apparatus 10 (i.e. the radiated power from the LED 14 is stabilized).

Because the photodiodes 26 and 94 in these two channels tend to track each other, the variation due to temperature and/or power supply is minimized by using the feedback channel. If desired, the temperature of the apparatus 10 can be measured and recorded using a thermistor 112 connected to an ADC input 114 of the microcontroller 56. A display (not shown) connected to the microcontroller 56 provides a user with a visible readout of the concentration measurements of the solution 46 contained in the sample container 42 (either water concentration or solvent concentration, or both can be displayed).

In alternative embodiments, a second measurement channel (not shown) could be added to the apparatus 10 by duplicating the first measurement channel and using the second measurement channel (with a sample container 42) to measure the absorbance in the sample solution 46 at a reference point that is not sensitive to water (e.g. at 1050 nm). This would allow the controller 30 to take a reading at both the 1450 nm and the 1050 nm absorbance bands. By taking the difference of the two readings, it is possible, for example, to minimize the effect of some defects which affect both wavelengths, such as scratches on the outside of the sample container 42.

In the preferred embodiment, the sample container 42 is a closed sample tube. Preferably, the sample tube is a vial-like container closed at one end and comprised of plastic, since most plastics are free of absorption bands in the NIR region. For example, the polypropylene Matrix 2D barcoded storage tubes available from Thermo Scientific are acceptable sample tubes for use as the sample container 42.

In general, the sample tubes can be comprised of any type of plastic, glass or other material that is free of NIR absorption bands, and that does not react with DMSO or whatever organic solvent solution is being analyzed. Stated differently, the sample container 42 should be transparent to near infrared radiation, meaning that it doesn't significantly absorb light in the 780 nm to 3000 nm wavelength range. More particularly, the sample container 42 does not absorb light in the 1300 nm to 2000 nm wavelength range. Typically, the sample tubes will have some type of cap, such as a screw cap, that covers the open end of the sample tube, so that the solvent (e.g. DMSO) contained within the sample tube can be protected from moisture and other contaminants, and so that evaporation of the solvent can be reduced.

In other embodiments, the sample container 42 may comprise another type of container. For example, the sample container 42 may comprise a piece of cylindrical tubing. For example, in compound storage facilities or laboratories, there are applications where a large amount of DMSO is dispensed to storage tubes or other equipments through tubing referred to as a transport tube. It is desirable to monitor the concentration or the water content of the DMSO in these transport tubes. The concentration of DMSO can be monitored by passing the transport tubing through the sample container holder 22 and through the hole 27. The tubing may hold stationary sample or may carry sample that is flowing through the tubing.

The concentration of the DMSO can be monitored in real time while the DMSO sample is flowing through the transport tubing. The transport tubing is preferably comprised of a plastic, such as polypropylene, since most plastics are free of absorption bands in the relevant NIR regions. However, other types of tubing, including plastics, silicone. PVC, polyurethane, fluoropolymer, polytetrafluoroethylene, thermoplastic elastomer or plasticizer free tubing, and including Tygon® and Teflon® brand tubing comprised of these materials, can be used as the cylindrical tubing, provided that the materials are free of absorption bands in the relevant NIR regions (i.e. 1450 and/or 1900 nm) and do not react with the sample solution.

In another embodiment, the sample container 42 may comprise a well plate containing a plurality of wells for holding the sample solution 46. For example, suitable well plates include plates having a well plate density of 96, 384, 1536 and 3456 (density meaning the number of wells contained on each well plate). Suitable well plates are comprised of chemically inert materials, such as polypropylene, polystyrene or cyclo olefin copolymer. In this embodiment, the absorbance measurement would be measured from the top of the well to the bottom of the well, or vice versa.

The sample container holder 22 can be made in a variety of sizes so that sample containers 42 of a variety of sizes (outer diameter and length) and/or shapes can be accommodated by the apparatus 10. Additionally, using memory in the microcontroller 56, calibration data can be stored and used for samples contained in sample containers of different sizes and/or shapes. Similarly, calibration data can be stored and used for samples in different solvents.

With the LED 14 being the main power consuming component, the apparatus 10 draws very little power. Furthermore, the LED 14 and many of the electrical components can be turned off and put into sleep mode when not in use. The low power consumption of the apparatus 10 allows the device to be operated from a battery or a DC power supply. Alternatively, the apparatus 10 can be powered through a universal serial bus (USB) associated with a computer or other electrical device. In addition to consuming very little power, the apparatus 10 also has a very quick measurement time. When the apparatus 10 is active in measurement mode, the measurement time is the sum of the A/D conversion time, computation time, and data transmission time. A typical measurement time is in the millisecond (ims) range. The low power consumption and the quick measurement time of the apparatus 10 make the apparatus 10 well-suited for use in stand-alone instruments, handheld devices and automated lab systems.

In a preferred embodiment, the apparatus 10 comprises the infrared LED 14 for emitting NIR light; the laser diode collimator 18 for forming a collimated light beam from the light emitted by the LED; the sample container holder 22 for holding the sample to container 42 in position so that the collimated light beam passes through the sample container when the sample container is held in the sample container holder; the first photodiode 26 for generating a first output signal that is related to the intensity of the collimated light beam after the collimated light beam has passed through the sample solution 46; and a control means for controlling the stability of the NIR light emitted by the LED 14. The first output signal is the current generated by the first photodiode 26. Controlling the stability of the NIR light emitted by the LED 14 means to insure that the radiated power from the LED 14 remains at constant level, despite temperature and/or power supply variations in the apparatus 10.

Preferably, in the control means, the LED light is sampled with the light pipe 53 and the second photodiode 94, and the feedback voltage is measured at ADC input 57 with an A/D converter inside the microcontroller 56 to generate a measured control voltage. Based on the measured control voltage, the microcontroller 56 changes the duty cycle of the PWM signal to affect the current and the light emitted from the LED 14, so that the light emitted by the LED 14 has a constant intensity. Preferably, the control means comprises a microcontroller that generates a pulse width modulation signal to control the current flowing through the infrared LED. More preferably, the control means comprises the microcontroller, a light pipe which samples a portion of the light emitted by the infrared LED, and a second photodiode for generating a second output signal that is related to the intensity of the light emitted by the infrared LED and that is used to set the pulse width modulation signal.

In a preferred embodiment, the method for determining the water content in an organic solvent solution comprises the steps of generating near infrared light using an LED that emits light having a wavelength that can be used to excite at least one absorption band in water; generating a collimated beam of light by directing the near infrared light from the LED through a laser diode collimator; positioning a sample solution comprised of an organic solvent so that the collimated beam passes through the sample solution; generating a photodiode signal by positioning a first photodiode to detect the collimated beam after it passes through the sample solution; converting the photodiode signal to a transmitted power signal; and using the transmitted power signal in a calculation to determine the absorbance of water in the sample solution.

The apparatus 10 provides a system and a method for measuring the water content of certain organic solvent solutions that is inexpensive, accurate and fast. Additionally, the measurements are made in the storage container so there is no extra contact with the sample solution, and consequently no contamination of the sample solution. Furthermore, no sample preparation is required.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

We claim:

1. An apparatus comprising:
    an infrared LED for emitting near infrared light;
    a laser diode collimator for forming a collimated light beam from the near infrared light emitted by the infrared LED;
    a sample container holder for holding a sample container containing a sample solution in position so that the collimated light beam passes through the sample solution when the sample container is held in the sample container holder;
    a first photodiode for generating a first output signal that is related to the intensity of the collimated light beam after the collimated light beam has passed through the sample solution; and
    a control means for controlling the stability of the near infrared light emitted by the infrared LED.

2. The apparatus of claim 1 wherein the control means comprises a microcontroller that generates a pulse width modulation signal to control the current flowing through the infrared LED.

3. The apparatus of claim 2 further comprising:
    a light pipe which samples the near infrared light emitted by the infrared LED; and
    a second photodiode for generating a second output signal that is related to the intensity of the near infrared light emitted by the infrared LED and that is used to set the pulse width modulation signal.

4. The apparatus of claim 1 wherein the LED emits light having a wavelength that can be used to excite at least one absorption band in water in the near infrared region.

5. The apparatus of claim 4 wherein the LED emits light having a peak wavelength centered at 1450 nm or 1900 nm.

6. The apparatus of claim 1 wherein the first photodiode comprises an InGaAs PIN photodiode.

7. The apparatus of claim 1 further comprising:
a first transimpedance amplifier that converts the first output signal to a measurement voltage signal.

8. The apparatus of claim 7 wherein the microcontroller makes an analog to digital conversion of the measurement voltage signal to yield a digital value.

9. The apparatus of claim 8 further comprising:
calculation means for calculating absorbance using the digital value.

10. The apparatus of claim 9 wherein the calculation means comprises an algorithm executed by a microcontroller.

11. The apparatus of claim 1 wherein the sample container comprises a material that is transparent in the near infrared region.

12. The apparatus of claim 11 wherein the sample container comprises a sample tube or a piece of tubing.

13. A method comprising:
generating near infrared light using an LED that emits light having a wavelength that can be used to excite at least one absorption band in water;
generating a collimated beam of light by directing the near infrared light from the LED through a laser diode collimator;
positioning a sample solution comprising an organic solvent so that the collimated beam passes through the sample solution;
generating a photodiode signal by positioning a first photodiode to detect the collimated beam after it passes through the sample solution;
converting the photodiode signal to a transmitted power signal; and
using the transmitted power signal in a calculation to determine the absorbance of water in the sample solution.

14. The method of claim 13 further comprising:
using a pulse width modulation signal to control an intensity of the near infrared light generated by the LED.

15. The method of claim 14 further comprising:
using a light pipe to sample a portion of the near infrared light emitted by the infrared LED; and
using a second photodiode to generate an output signal that is related to the intensity of the near infrared light emitted by the infrared LED and that is used to set the pulse width modulation signal.

16. The method of claim 13 wherein the organic solvent comprises DMSO.

17. The method of claim 13 wherein the calculation utilizes the equation $A = \log_{10}(P_{solvent}/P_{solution})$.

18. The method of claim 13 wherein the sample is contained in a sample container that is transparent to near infrared light.

19. The method of claim 13 wherein the LED has a power spectrum that closely matches one of the absorption bands of the water absorption spectrum in the near infrared region.

* * * * *